US006852282B2

(12) United States Patent
Miyake et al.

(10) Patent No.: US 6,852,282 B2
(45) Date of Patent: Feb. 8, 2005

(54) CHEMICAL ANALYZER AND CHEMICAL ANALYZING SYSTEM

(75) Inventors: Ryo Miyake, Tsukuba (JP); Naruo Watanabe, Chiyoda (JP); Hajime Katou, Chiyoda (JP); Takao Terayama, Ushiku (JP); Yasushi Nomura, Mito (JP); Hiroshi Mitsumaki, Mito (JP)

(73) Assignee: Hitachi, Ltd., Tokyo (JP)

( * ) Notice: Subject to any disclaimer, the term of this patent is extended or adjusted under 35 U.S.C. 154(b) by 278 days.

(21) Appl. No.: 10/121,734

(22) Filed: Apr. 15, 2002

(65) Prior Publication Data

US 2002/0110488 A1 Aug. 15, 2002

Related U.S. Application Data

(63) Continuation of application No. 09/526,565, filed on Mar. 16, 2000, now Pat. No. 6,383,452.

(51) Int. Cl.[7] .............................................. G01N 35/00
(52) U.S. Cl. ........................ 422/63; 422/64; 422/67; 422/70; 422/81; 422/101; 422/104; 436/180
(58) Field of Search ........................... 422/63, 64, 67, 422/70, 81, 101, 104; 436/180, 177

(56) References Cited

U.S. PATENT DOCUMENTS

| | | | |
|---|---|---|---|
| 4,108,062 A | 8/1978 | White | |
| 4,200,607 A | 4/1980 | Suzuki | |
| 4,237,234 A | 12/1980 | Meunier | |
| 4,451,433 A | 5/1984 | Yamashita et al. | |
| 5,246,665 A | 9/1993 | Tyranski et al. | |
| 5,422,079 A | 6/1995 | Parekh et al. | |
| 5,519,635 A | 5/1996 | Miyake et al. | |
| 5,563,042 A | 10/1996 | Phillips et al. | |
| 5,690,895 A | * 11/1997 | Matsumoto et al. | .......... 422/73 |
| 5,695,720 A | 12/1997 | Wade et al. | |
| 6,193,933 B1 | 2/2001 | Sasaki et al. | |
| 6,197,255 B1 | 3/2001 | Miyake et al. | |
| 6,383,552 B1 | * 5/2002 | Noecker et al. | .............. 427/2.3 |

FOREIGN PATENT DOCUMENTS

| | | |
|---|---|---|
| JP | 55-60854 | 5/1980 |
| JP | 57-082769 | 5/1982 |
| JP | 03-223674 | 10/1991 |
| JP | 9-504732 | of 1997 |

* cited by examiner

*Primary Examiner*—Ana M. Fortuna
(74) *Attorney, Agent, or Firm*—Antonelli, Terry, Stout & Kraus, LLP (57) ABSTRACT

A chemical analyzer for measuring a concentration of components of a sample liquid, by mixing the sample liquid with reagents, so as to react the reagents upon the components thereof, includes a carrier having an introducing portion through which the sample liquid is injected, passages for distributing the sample liquid injected from the introducing portion, and plural reactor portions which hold the sample liquid therein to be mixed with the reagent, thereby to react. A movable driver portion is provided on which the carrier is mounted and a reagent charging device is provided for ejecting the reagents which are different for the respective plural reactor portions of the carrier, sequentially. Further, a detector is provided for detecting the components after mixing the reagents with the sample liquid.

9 Claims, 8 Drawing Sheets

CHEMICAL ANALYZER AND CHEMICAL ANALYZING SYSTEM

CROSS REFERENCE TO RELATED APPLICATION

This is a continuation of U.S. application Ser. No. 09/526,565, filed Mar. 16, 2000, now U.S. Pat. No. 6,383,452, the subject matter of which is incorporated by reference herein.

BACKGROUND OF THE INVENTION

The present invention relates to a chemical analyzer or chemical analysis apparatus for analyzing components of a liquid of a living body, such as blood and/or urine, a water, etc., and in particular to the chemical analyzer being suitable for use of a so-called POC (Point-of-Care) testing, i.e., an urgent testing in an operation room or in a scene of urgency, a home or bed side testing, a quick testing beside a patient in a general medical clinic.

A chemical analyzer for the liquid of a living body, according to the conventional art, is disclosed and known, for example in U.S. Pat. No. 4,451,433. The apparatus is constructed with a calorimetric measurement portion for analyzing and/or determining the quantity of components, such as proteins and enzymes in blood and in urine, and an ion analyzing portion for analyzing ions in blood. This apparatus has a processing speed or velocity of performing several hundred tests per an hour, and a large-sized one has that more than 9,000 tests. In particular, in the system, for increasing up the processing speed in the calorimetric measurement portion, a large number of reactor vessels or cells are provided on a circumference of a turn table, upon an upper surface of the main body of the chemical analyzer, thereby to conduct mixing, reacting and measurement of blood samples, sequentially, through the overlapping processes thereof.

Main elements constructing such the apparatus are an automatic sample/reagent supply mechanism for supplying sample liquids and agents to the reactor vessels, a reservoir portion for keeping containers of several-ten kinds of reagents therein, an automatic mixing mechanism for mixing the blood sample and the reagent in the reactor vessels, a measurement device for measuring properties of the blood samples which are under or have been completed with the reaction thereof, an automatic washing or rinsing mechanism for sucking and discharging the blood samples completed with the measurement thereof and for washing or rinsing the reactor vessels, an automatic washing or rinsing mechanism of the automatic sample/reagent supply mechanism for reducing mutual contamination between the blood samples due to deferring or carrying-over thereof and/or contamination between the different reagents, and a controller portion for controlling operations of those.

There are several-tens of kinds items of colorimetric measurements to be objected, and as the items in an ordinary test are, the analysis must be conducted on at least ten or more kinds of items for each one of the samples. For conducting the analysis of those items by means of only one apparatus, the reagent supply mechanism must be provided with a mechanism, such as a so-called reagent pipetting mechanism, with which the reagent is selected from a plurality of reagent containers to be supplied into the reactor vessels, sequentially, by a predetermined amount thereof. The reagent pipetting mechanism is constructed to mainly comprise a nozzle for sucking the reagent inside to hold it therein, a mechanism for moving the nozzle in a three-dimensional manner, and a suction/discharge control pump for sucking and/or discharging the reagent into and/or from the nozzle.

Also, as the conventional art, in particular for use in the POC testing, a blood analyzing apparatus is described in Japanese Patent Laying-Open No. Hei 9-504732 (1997) of PCT application No. PCT/US94/10299 (Publication No. WO95/06870). This analyzer comprised an optical detector, a main body of analyzer for performing control, signal processing, signal input/output, etc., and a disposable type of centrifugal reagent rotor portion(s) for performing adjustment for pre-processing with the reagent by introducing the sample liquid therein. First, the blood as the sample is injected into a guide or introduction opening which is provided at a central portion of a disc. After setting the rotor into the main body, the rotor is driven rotationally by an operation of the main body. In this instance, serum components are divided or separated from by means of the centrifugal function, so as to be determined in quantity by a predetermined amount of serum, and are mixed with a diluting liquid which is maintained inside the rotor. Further repeating stoppage and rotation of the rotor, the diluting liquid is introduced into the twelve (12) pieces of the reactor vessels which are provided around thereof. In each of the reactor vessels is already contained a dried reagent, which is corresponding to the respective different items of measurement, and also a ball for mixing, thereby mixing the reagent and the diluting liquid so as to start a predetermined reaction therebetween. After about twelve (12) minutes, an optical absorbance within the vessel is measured by the optical detector which is built-in within the main body. Those reagent rotors are prepared for several kinds thereof, corresponding to combinations of the items of measurement.

Requirements are made to such the analyzing apparatus for use in the POC testing, that it is small in sizes and portable, that the analysis results can be obtained quickly therefrom, that it is easy in handling thereof, that there is almost no necessity of maintenance for enabling or starting the analysis therewith at any time, and further that it is able to have a sufficient competitiveness in the cost, in particular, comparing to a testing by asking or requiring to a test center with charge, even in a case where it is used routinely for the testing nearby the patient, in a medical clinic or the like.

Therefore, there are problems listed below, in particular when applying the analyzing apparatus of the conventional arts mentioned above into the POC testing.

First, with the first conventional art, since the apparatus is large in the size, generally it is difficult to be provided or located, such as, in a scene of urgency or in an operation room where a space therein is limited or restricted. Also, since it is provided fixedly through conduits for the washing and disposal liquids, then it is impossible to be moved or carried nearby the patient staying at home and/or to bed side. Further, for using such the apparatus in the medical clinic and so on, a running cost, including the cost of the apparatus itself and the maintenance fee thereof is large, therefore the apparatus is not in economic.

Next, the chemical analyzer according to the second conventional art, it can be provided or located in such the operation room, etc., since it is small in the size, comparing to the large-sized chemical analyzer according to the first conventional art. Also, all the portions through which the sample liquid conducts with are made disposable, therefore there is no need of supplying the washing liquid to the conduits. Accordingly, the apparatus is relatively easy to be carried or moved and is preferable from a view point of maintenance thereof. And, it also has a feature that the cost of the apparatus itself is low. By the way, in the reagent rotor is contained the reagent(s) in advance, for use in measurement of the items which are made or determined by a maker thereof, therefore, there occur actually many cases where the measurement is made also on the unnecessary item(s) therein at the same time. Accordingly as will be mentioned in the following, there are problems in aspects of the quickness and the cost thereof, in particular relating to the POC testing.

First of all, even when there is a combination of the items required to be measured depending upon the condition of the patient in an urgent test, the analysis must be conducted sequentially by changing the several reagent rotors alternatively, if no reagent for such the combination is contained in that reagent rotor, as a result of this, it takes an excessive time. This comes to be a big problem in the urgent testing where the test result is required to be outputted quickly.

Second, since the items in analysis are already determined fixedly, the analysis is conducted even on the item which is inherently unnecessary to be analyzed, and the reagent rotor, which was used once for another measurement, must be disposed, even in a case where the unnecessary analysis must not be conducted. Therefore, it costs excessively, and is economically inferior in competitiveness of the cost, comparing to the testing by requiring to the test center mentioned above. At the present time, where a further suppression in the testing cost comes to be a very important factor due to reduction of medical expense, the above becomes a bottleneck for spreading the use of such the chemical analyzer widely, such as at home, bedside, in the medical clinics, etc.

OBJECT AND SUMMARY OF THE INVENTION

An object, according to the present invention, is to provided a chemical analyzer, being small-sized and portable, wherein the reagents can be set or determined by the user freely, depending upon the items to be analyzed, and without necessity of conduits for the washing and disposal liquids, thereby being free or easy in the maintenance thereof.

The object mentioned above is dissolved, according to the present invention, by a construction wherein an analyzing cassette is constructed by forming one introduction opening for introducing a sample liquid to be tested on one piece of a substrate, so that the introduced sample liquid is divided into a plurality of flow passages and is sent to a plurality of reactor portions, which are provided at the end portion of the flow passages, respectively, after being measured by an amount of liquid to be used for an analysis in a measurement portion which are provided on the ways of the flow passages, and into the reactor portions mentioned above are supplied reagents corresponding to the items of testing in an analyzer portion which is provided separately therefrom, thereby conducting analysis after mixing the reagents and the sample liquid.

Further, a filter is provided in the introduction portion of the analyzing cassette, so that the sample liquid, such as in a condition of serum, is sent into the reactor portions, for example, when blood is supplied with.

Also, the analyzer portion holds the analyzing cassette therein, and has a positioning mechanism for supplying the reagent(s) required into the reactor portions of the analyzing cassette mentioned above. Further, it may be constructed so that, by means of this positioning mechanism may be also achieved shifting or removing up to a position where the analysis is actually conducted.

DESCRIPTION OF PREFERRED EMBODIMENTS

Figure 1:
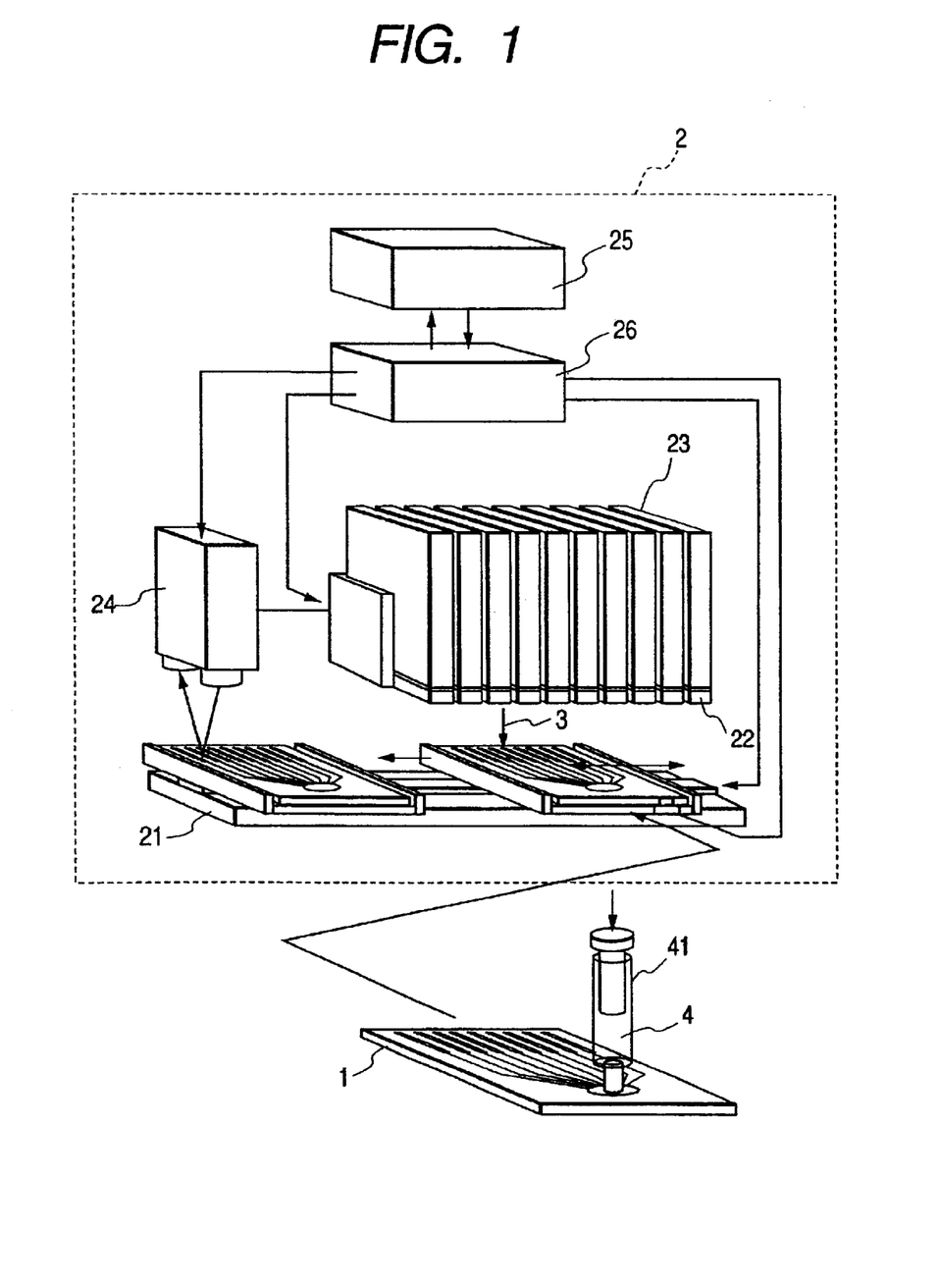
FIG. 1 shows the construction of a chemical analyzer according to the present invention.
Figure 2A:
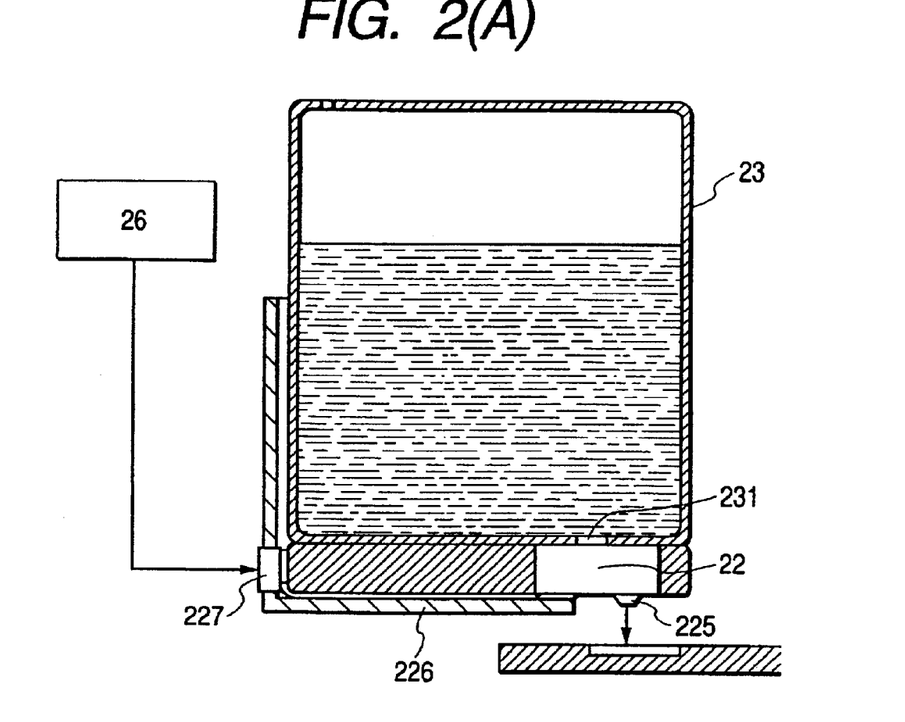
FIGS. 2(A) and 2(B) show cross-section views of a sample supply mechanism and a sample scale pump of the present invention.
Figure 2B:
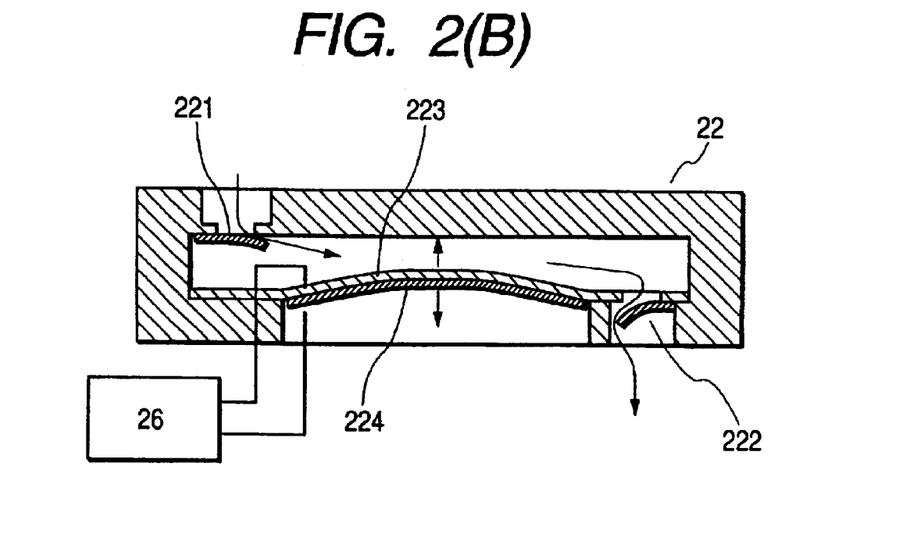
Figure 3A:
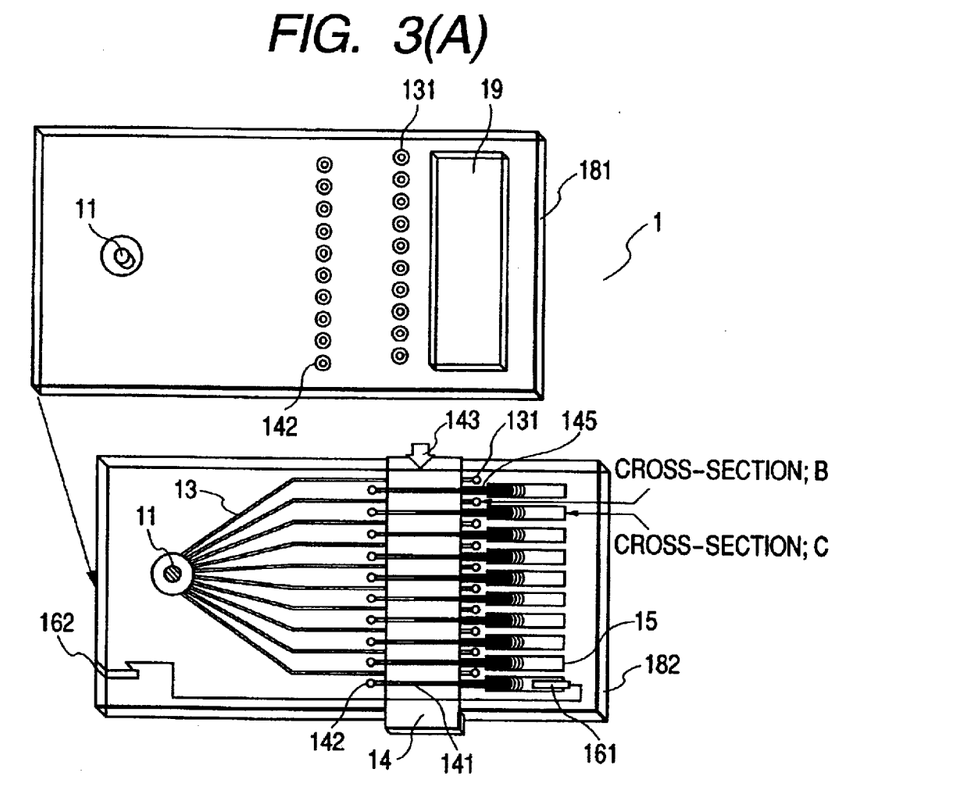
FIGS. 3(A), 3(B) and 3(C) show the construction of an analyzing cassette according to the present invention, and the cross-section views of portions indicated by an arrow B and an arrow C in the FIG. 3(A)
Figure 3B:
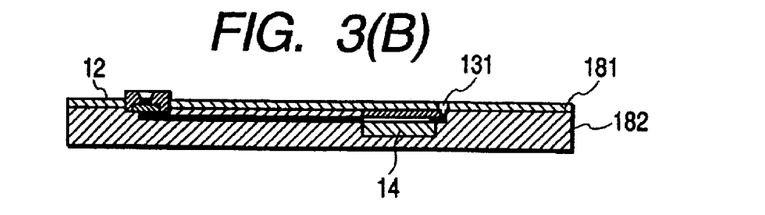
Figure 5A:
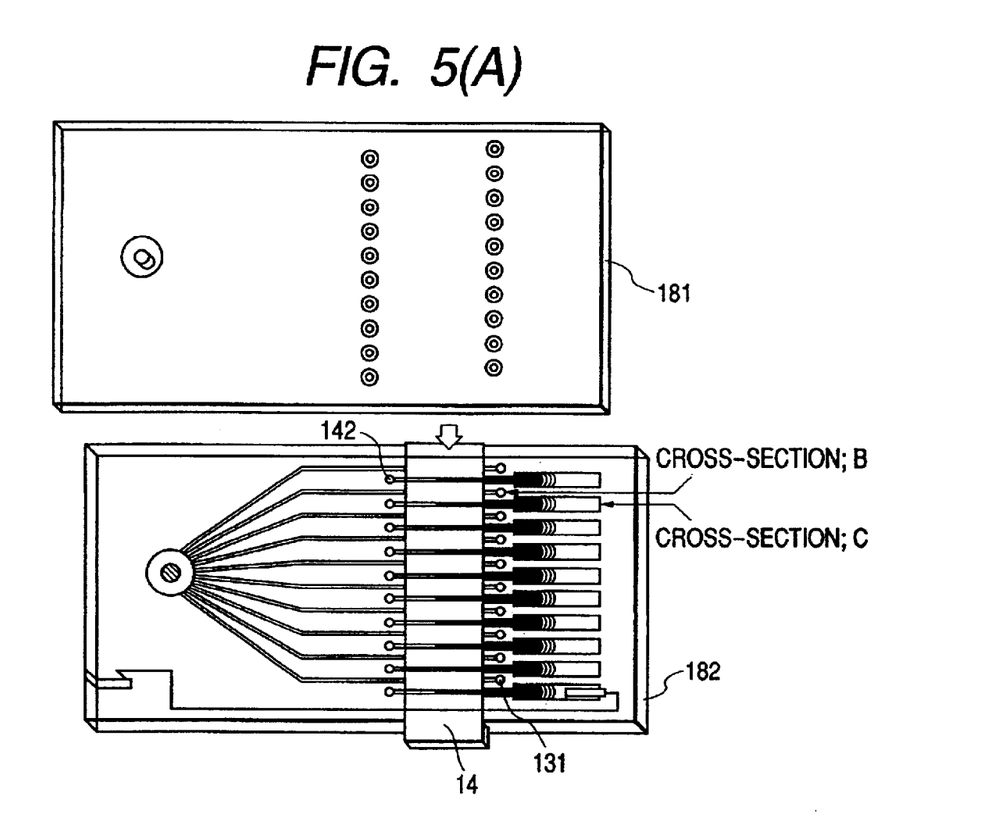
FIGS. 5(A) shows the construction of an other analyzing cassette according to the present invention, and FIGS. 5(B) and (C) are for explaining the operation of that shown in the FIG. 5(A)
Figure 6A:
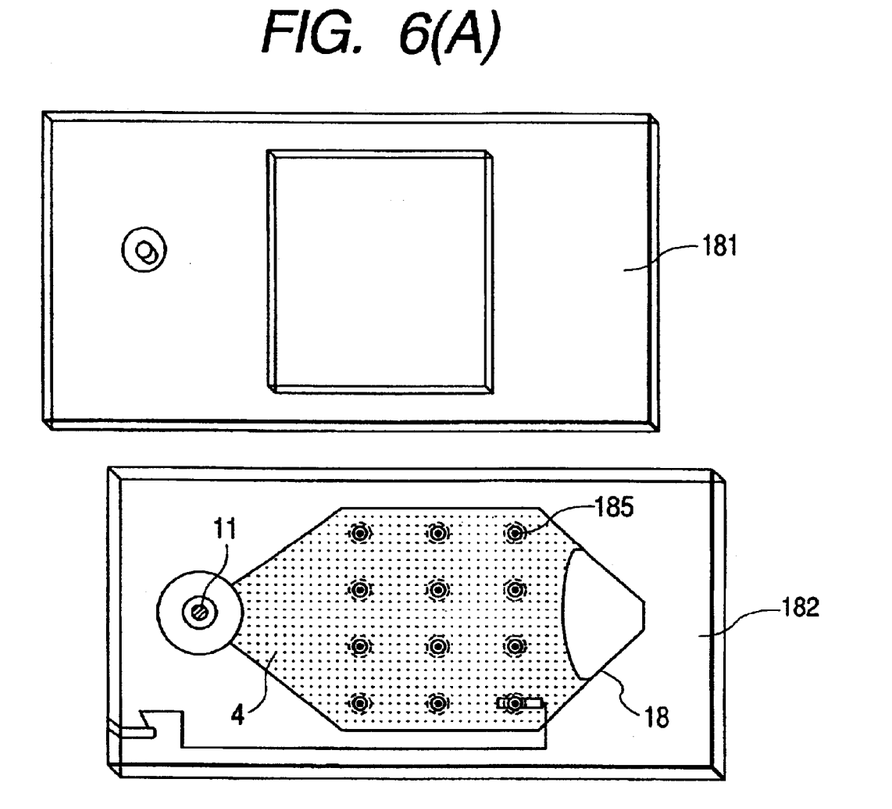
FIGS. 6(A) shows the construction of a further other analyzing cassette according to the present invention, and FIG. 6(B) the cross-section view at the center portion of that shown in the FIG. 6(A)
Figure 6B:
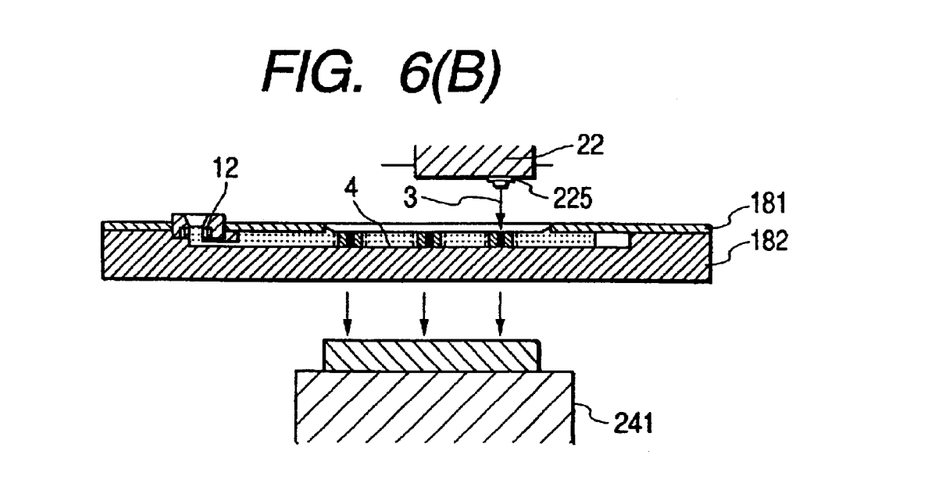
Figure 7:
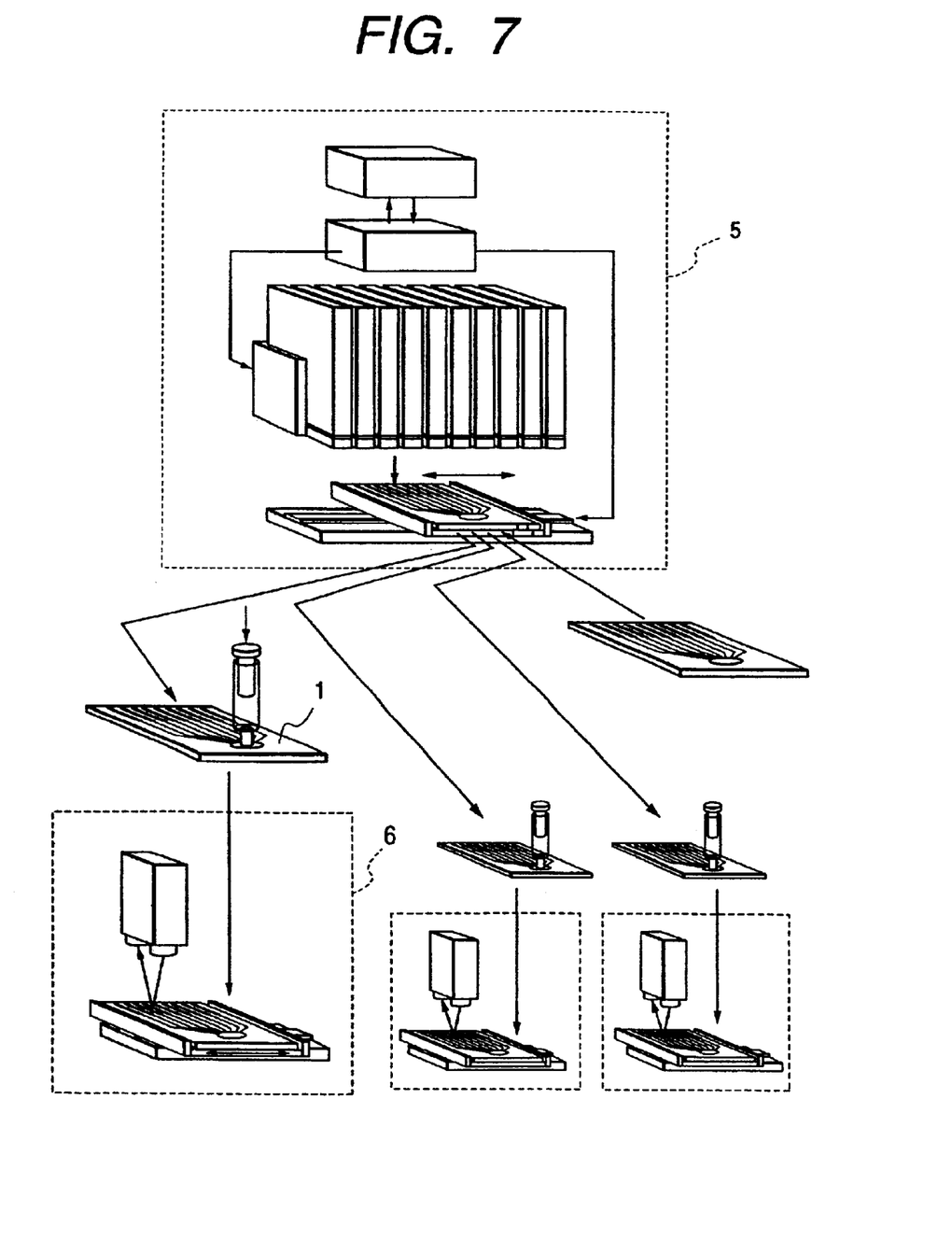
FIG. 7 shows the construction of a chemical analysis system of another embodiment according to the present invention.
Figure 8:
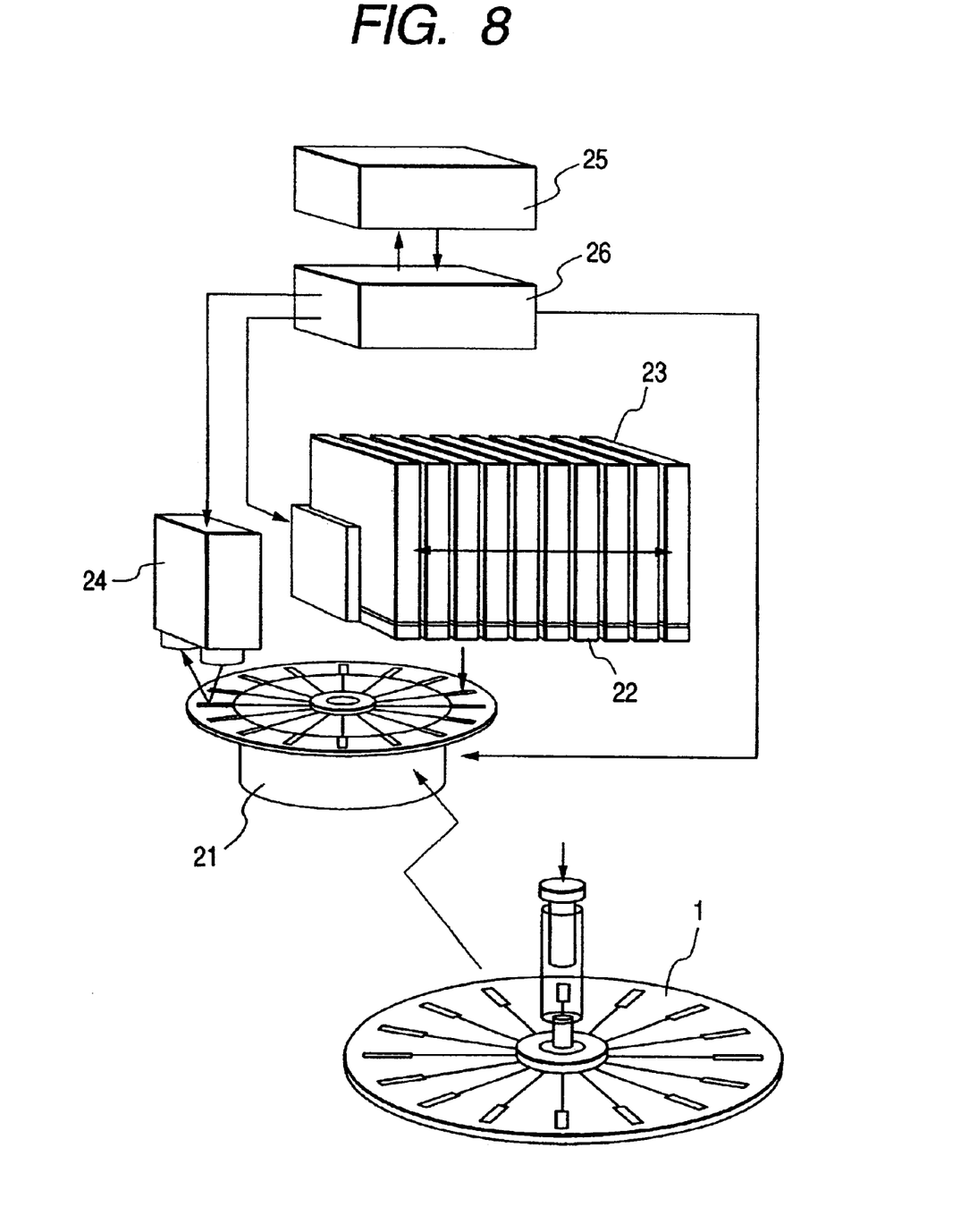
FIG. 8 shows the construction of a chemical analyzer of another embodiment according to the present invention.

Hereinafter, embodiments according to the present invention will be fully explained by referring to the attached drawings, in particular the FIGS. 1 to 3. Here, the FIG. 1 shows the total construction of the chemical analyzer according to the present invention; FIGS. 2(A) and 2(B) for explaining the reagent scale pump which is used in the present invention; FIGS. 3(A), 3(B) and 3(C) the construction of a disposable type of analyzing cassette; FIG. 4(A) shows the construction of another analyzing cassette according to the present invention, and FIGS. 4(B) to (E) are for explaining the operation of that shown in the FIGS. 4(A) to (E) through FIGS. 6(A) and (B) show the constructions of other analyzing cassettes according to the present invention; and the FIGS. 7 and 8 shows the total constructions of another embodiment according to the present invention.

Explanation will be given on the construction of the chemical analyzer according to the present invention, by referring to the FIGS. 1 to 3. The FIG. 1 is a view of showing the total structure and positioning of elements of the present chemical analyzer from an upper oblique position.

The chemical analyzer according to the present invention is constructed with mainly two elements. Namely, an analyzing cassette 1, i.e., a carrier comprising an area for holding the disposable reagents and sample liquid thereon temporally and being formed from a transparent material, and a main body 2 of analyzer into which the analyzing cassette 1 is inserted. The analyzer main body 2 includes a carrier engagement portion into which the analyzing cassette can be inserted in a manner of a drawer, and is composed from a linear driver portion 21, i.e., as a position adjustment device for adjusting the positions by shifting that including the carrier engagement portion, for the purpose of adjusting the position of the analyzing cassette inserted, a line of reagent bottles 23 including a reagent scale and discharge pump 22, i.e., as the reagent discharging device being positioned in an upper portion of the liner driver portion 21 and for discharging the reagent by a predetermined amount thereof into an analyzing cassette 1, an optical detector 24 provided at the most left-hand side of the linear driver portion 21, a signal processor 25 for recording information in relation with, such as, setting of the analysis items, an order in positions of the reagent bottles 23, etc., and for conducting display and record of the analysis results, and a controller 26 receiving an instruction of an operation process from the signal processor 25 for sending out control signals to the liner driver portion 21, the reagent scale and discharge pump 22 and the optical detector 24, etc. The reagent 3 is supplied from the reagent scale and discharge pump 22 into the analyzing cassette 1 which will be mentioned in details, later.

Next, explanation will be given on the structure of the reagent scale and discharge pump 22 and the reagent bottles 23 being attached or equipped therewith, according to the present embodiment, by referring to the FIGS. 2(A) and (B). On the bottom portion of the reagent bottle 23 is provided an opening 231. In manner of connecting with the opening 231 is provided the reagent scale and discharge pump 22 of a type of a diaphragm, shown in the FIG. 2(B). On the reagent scale and discharge pump 22 are provided check valves 221 and 222, at an inlet and an outlet thereof, each of which flows liquid only in one direction therethrough. Also, a diaphragm 223 is provided in a pumping chamber, on an outer surface of which is attached a vibration plate 224. At both ends of this vibration plate 224 are provided wirings for supplying with voltage thereto. The outlet of the diaphragm type of reagent scale and discharge pump 22 is opened directing below, and is provided with a nozzle 225 for making a flow discharging smoothly. The wirings of the vibration plate 224 are connected through driving wirings to an electric contact point 227 which is provided within a holder 226.

Next, explanation will be given on the structure of the analyzing cassette 1 according to the present invention, by referring to the FIGS. 3(A) to (C). Roughly, the analyzing cassette 1 is constructed with two (2) pieces of substrates. The one is a substrate 182 for use in detection, including a reactor cell 16, etc., thereon, and the other is an upper substrate 181 which is provided in an upper portion of that substrate 182 for use in detection. The analyzing cassette has sizes of 55 mm in width and 90 mm in length, i.e., a so-called a size of a name card.

On the upper substrate 181 are provided a guide opening 11' for fitting to an injector for injecting the sample liquid, air openings 131' and 142' for communicating with fine openings 131 and 142, which are provided at end portions of fine flow passages 13 and 145, respectively, for use in taking-out of the air included therein, and a cutting portion 19, through which the reagents are supplied into the reactor portions, and for use of detection in conducting the analysis thereof. This upper substrate 181 is fixed on the substrate 182 for use in detection by means of, such as, an adhesive.

On the substrate 182 for use in detection of the analyzing cassette 1, according to the present embodiment, a distribution portion is provided. In the distribution portion is provided an introducing portion 11 for one sample, so as to introduce the sample liquid therein. The introducing portion 11 is communicated with an introducing opening 11' of the upper substrate 181. In a lower portion of the introducing portion 11 is provided a filter 12 for giving a flow resistance to the components of blood corpuscle or cell, thereby to pass them through with priority.

After the filter 12 which constructs the distribution portion, fine flow passages are provided on a side of the substrate, being divided into a plurality thereof. In the present embodiment, ten (10) pieces of the fine flow passages 13 are provided, and are opened into the air through the fine openings 131' formed in the upper substrate 8. Though the distribution portion is constructed to cover up to the filter 12 in the present embodiment, however the filter 12 may be provided on the side of the substrate.

On the way of those fine flow passages 13, a detachable quantity determining valve 14 of a slide type is integrated therein, through which a predetermined amount of serum can be cut out by sliding thereof. Fine flow passages 141 within the valve are connected with the fine flow passages 13 to be injected into with the serum, until when they come to be filled up with the serum therein. When they are filled up with the serum, the valve as a whole is slid, so as to be fitted with another fine flow passages. The ends of the fine flow passages 145 in the side of an upper stream thereof are opened from the second fine openings 142 into the air through the fine openings 142' of the upper substrate 8. At the other ends of them in a lower stream side are provided testing papers 15 in regions or portions where the liquid are held or maintained. Here, the testing papers 15 may be made from a paper or a fibrous material, and they are sufficient as far as they can hold or keep the serum and the reagents therein, having a color of white and being made from a material showing moisture absorbance therewith. The testing papers 15 are extended as they are and is expanded or spread into the reactor cells 16.

The upper portion of the reactor cell 16 is formed as a window being opened. However, in the present embodiment, the portion of the upper substrate 8 opposing to the reactor cell 16 is cut to form a window 19 therewith. The cutting portion at the side of the upper substrate 8 is closed by a seal member when the analyzing cassette 1 is not yet used, thereby to protect from dusts, etc., entering into the reactor cells, and the cassette is so constructed that the seal is removed when it is used. It is needless to say that the portion opposing to the reactor cell 16 of the upper substrate 8 may be made into a window which can be opened by sliding thereof. Through this window 19, the reagent 3 is ejected or injected onto the testing paper 15. Among the ten (10) pieces of the reactor cells 16, an electrode 161 is provided within the cell which is located at the lowest side in the figure, for measuring an electrolyte in the serum, and is connected between the connector portion 162 through a signal line inside the cassette.

The present apparatus with the structure mentioned above operates as below.

First, the blood (total blood) 4 containing blood corpuscle or cells therein is sent out inside from the introduction portion 11 of the analyzing cassette 1 by means of the injector 41. In that instance, with the function of the filter 12 can enters the component of serum inside with priority rather than the component of blood corpuscle or cells. The serum component is pressured by the function of a pressure of the injector 41 and capillarity within the ten (10) pieces of the fine flow passages divided, and it is filled up with up to the first fine openings 131, passing through the fine flow passages 141. By a manual or automatic operation under this condition, an end of the quantity determining valve 14 of the slide type is pushed in a direction of an arrow 143 in the FIG. 3(B). Thereby, the portion of the fine flow passages 141 comes to be fitted with the other fine flow passages 145. Each the fine flow passage 141 in the slide type quantity determining valve 14 is constant in the volume thereof, thereby performing a quantitative sampling with high accuracy. In the present embodiment, the sizes in volume of the each fine flow passage 141 in the slide type quantity determining valve 14 are 0.2 mm square, and the flow passage of length 7.5 mm is formed, thereby a very small quantity of serum of 0.3 µl is sampled for determining quantity with the high accuracy. Of course, the amount of sampling can be set freely or arbitrarily by adjusting the sizes of the above-mentioned fine flow passages 141.

The constant amount of serum inserted in each of the fine flow passages 141 within the slide type quantity determining valve 14 is absorbed by the end of the testing paper laying at another exit, and is spread equally or uniformly up to the portion of the testing paper 15. At this time point, the serum 4 which is determined in the quantity thereof is in a condition that it penetrates into each of the testing papers 15 inside the analyzing cassette 1. This analyzing cassette 1 is set into the linear driver portion 21 of the main body 2 of the apparatus.

When an input of a starting is applied from the signal processor 25, the reagent bottles 23 are selected sequentially among the group of the reagent bottles, in the order of measurement items which are set up in advance, and the reactor cells 16 of the analyzing cassette 1 are moved into a lower portion thereof by means of the linear driver portion 21. After that, upon the control signal of the controller 26 is operated the reagent scale and discharge pump 22 which is provided below the reagent bottles 23, thereby the predetermined amount of reagent 3 is injected aiming upon a piece of the testing paper 15 in the reactor cell 16. With the same operation, the different reagents 3 are also injected into the reactor cells 16 neighboring thereto, sequentially.

Into each of the ninth (9th) and tenth (10th) cells 16, a predetermined amount of a diluting liquid is injected. On the testing paper 15, since the reagent 3 is spread equally and uniformly by the function of capillarity, the reagent 3 and the serum 4 are mixed and reacted with almost equally and without spots. Leaving as they are under this condition, the reaction proceeds on each of the testing papers 15, and it starts emission of color or light. At every constant time period is operated the linear driver portion 21, so as to move the portion of the each testing paper 15 of the analyzing cassette 1 under the optical detector 24. In the optical detector 24, a spectral intensity and/or a luminous intensity on the testing paper 15 are measured at any time. With the ninth (9th) cell, an absorption spectrum of the diluted serum itself is detected. And, with the tenth (10th) cell, an ion concentration in the serum is detected by the electrolyte sensor 161. However, although the substrate is mentioned or explained to be formed from the transparent material in the present embodiment, it is also possible to make transparent only in a portion where the testing papers are set into, thereby to detect through the optical detector 24.

As was mentioned in the above, monitoring the reacting processes in the each reactor cell 16 by moving the linear driver portion 21 in parallel, appropriately, it is possible to make the measurement with an accuracy being equal to that made with a large-sized automatic analyzer. The analyzer cassette 1 completing in the measurement therewith is disposed.

As was mentioned previously, with the conventional chemical analyzer wherein the unit of a disposal type is used, the items of the measurement is already determined by the maker thereof. Because of this, the analysis must be repeated over a plurality of units or the measurement must be conducted even on unnecessary items until when the result of the combination of the items comes out for the analysis which are actually needed, therefore it is not in economic.

On the contrary to that, the disposal type of the analyzing cassette 1 is used in the chemical analyzer of the present embodiment, therefore it is possible to select the testing items arbitrarily and independently by the user thereof, without loosing the easiness in maintenance and handling and the portability thereof. Namely, the reagent bottles 23 are selected and are installed into the main body 2 of the analyzer, upon the items which are used frequently depending upon circumstances of use by the user. Next, it is possible to make the measurement, by further selecting the most suitable combination among the reagent bottles 23 before the analysis. Also, because all of the portion in which the blood is used (i.e., the analyzing cassette) is disposal or disposable, there is no necessity of processing by the washing or rinsing liquid and/or processing of the waste liquid, therefore the maintenance is easy. Further, as an effect according to the present embodiment, since the structure of the analyzing cassette 1 is same in shape, sizes and specifications, the cost of the cassette can be remarkably reduced by the mass-production thereof.

Next, explanation will be given on a second embodiment according to the present invention, by referring to the FIGS. 4(A) to (E).

The main body 2 of analyzer is same to the embodiment shown in the FIG. 1. It differs from the first embodiment in the methods of sampling for determining the quantity of the serum 4 in the analyzing cassette 1, and for supplying and detecting of the reagent. As is shown in the FIG. 4(A), in the analyzing cassette 1 of the present embodiment, a rotary valve 17 is provided following the induction portion 11 of the blood 4, thereby necessitating no such the slide type of the quantity determining valve 14. Namely, by forming distributing flow passages 171 in radial direction on the rotary valve 17, not only the dividing, but also the quantity determining is conducted therewith. When introducing the blood, the rotary valve 17 is in the condition that it is not connected with the fine flow passages 13, and it is rotated to be connected with the fine flow passages 13 when the blood is filled up with in the divided passages provided on the rotary valve 17.

As is shown in the FIG. 2(A), on the way of the fine flow passages 13 are provided portions 132, each of which extends in a step-wise manner. Being connected to those extending portions 132, there are provided the reactor cells 16. On upper portion of those extending portions 132 are formed thin films 162, respectively, so that the injector 226 can be dug or stuck into them easily. Also, in front or behind of the reactor cell 16 are provided reflection portions 163 for use in introducing and/or emitting a light into and/or from the reactor cell 16. Not only the radial distributing flow passage 171, but also passages 172 are provided on the rotary valve 17, for sending compressed air therethrough into the positions being symmetric thereto. Further, injectors are prepared for sending the compressed air. However, the rotation of the rotary valve 17 is explained to be conducted manually in the present embodiment, however there may be provided a mechanism for rotating the main body of the apparatus, automatically. And, the supply of the compressed air mentioned above may also be conducted automatically from the main body of the apparatus. In the present embodiment, the reagent scale and discharge pump 22 comprises the injectors 226 therein, for use in digging or sticking in the place of the nozzles. Also, the linear driver portion 21 of the main body 2 of the apparatus further comprises a mechanism in it, for elevating the analyzing cassette 1 therewith.

Figure 4A:
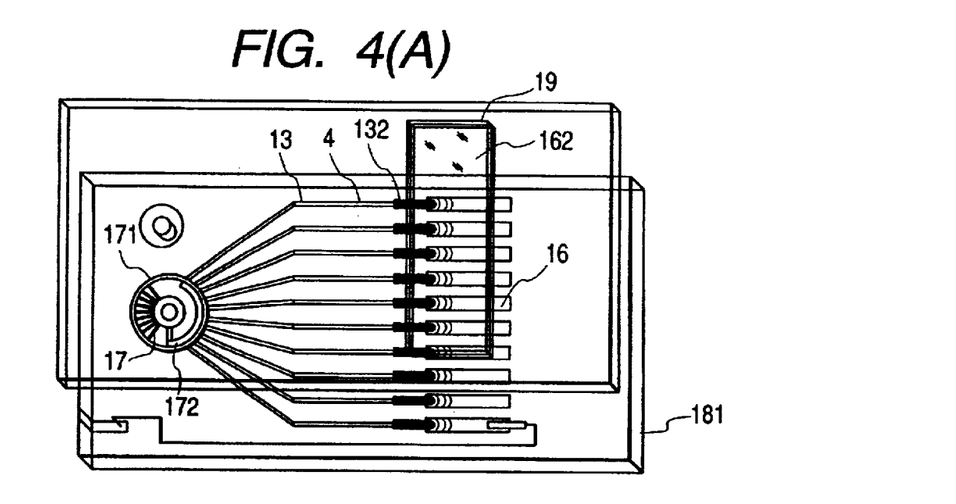
FIGS. 4(A) shows the construction of another analyzing cassette according to the present invention.
Figure 4B:
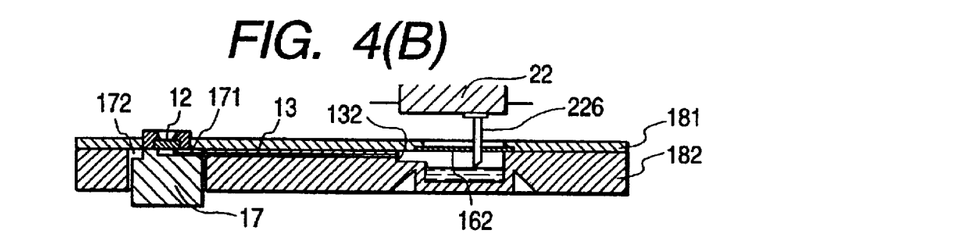
FIGS. 4(B) to (E) are for explaining the operation of that shown in the FIG. 4(A)

The apparatus having such the construction as mentioned above performs the following operation. First, the analyzing cassette 1 is set into the linear driver portion 21 of the main body 2 of the apparatus. The linear driver portion 21 shifts so that the reactor cells of the analyzing cassette 1 are located at the lower positions of the predetermined reagent bottles 23. Next, it is elevated upward, therefore the injector 226 for digging is stuck into the film 162 in the upper portion of the reactor cell 16. Under this condition, the reagent scale and discharge pump 22 is actuated and a predetermined amount of the reagent 3 is injected into the reactor cell 16 through the injector 22. This operation will repeated for the other nine (9) pieces the reactor cells, in the same manner.

Figure 4C:
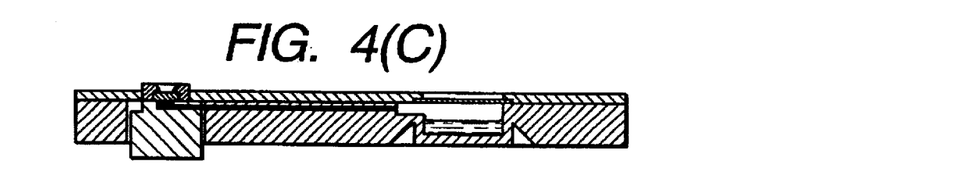
Figure 4D:
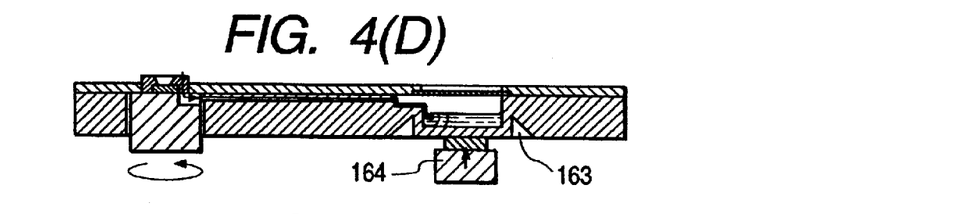

After that, as shown in the FIG. 4(C), the analyzing cassette 1 is taken out from the main body 2 of the apparatus, and it comes to be in touch with the injector 41, in which the blood as the sample liquid is filled up with, so as to be dripped into the introduction portion 11 of the sample. Only the serum of the blood is distributed into the fine flow passages 13 through the filter 12. The serum comes up to the step-wise portion 132 of the fine flow passages 13 by the capillarity thereof, but it stops it's proceeding due to the steps.

Figure 3C:
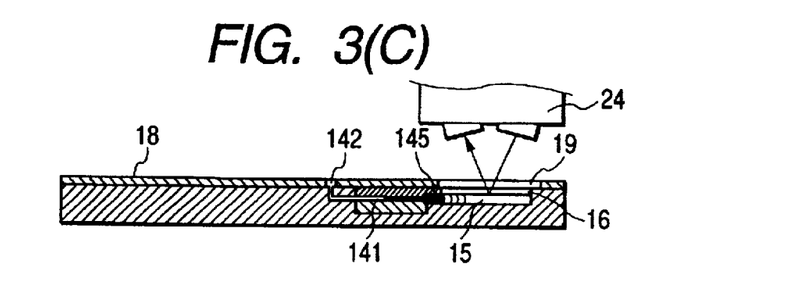

At that moment, as shown in the FIG. 3(C), the rotary valve 17 is rotated so that the fine flow passages 13 at the upper stream side thereof are turned to be connected to the passages 172 for the compressed air. Thereby, the serum 4 in each of the fine flow passages 13 is sampled by a predetermined amount thereof. Further, inserting the injector for sending the compressed air into the introducing portion 11 so as to send the air into the passage, the serum is discharged or ejected into each of the reactor cells 16. Due to flow of the serum discharged and power or force of the air following thereto, the mixture between the serum and the reagent is promoted.

Next, the analyzing cassette 1 is inserted into the linear driver portion 21 of the main body 2 of the apparatus, again. If the mixture is not sufficient in the previous operation, it may be in contact with a mixer 164 for emitting ultrasonic waves into the reactor cell, so that they are mixed acoustically therein, as shown in the FIG. 4(D), as the case may be. When it begins emission of color with progress of the reaction, the absorption spectrum or light emission within the sequential reactor cells 16 are detected, in the same manner as in the first embodiment.

Figure 4E:
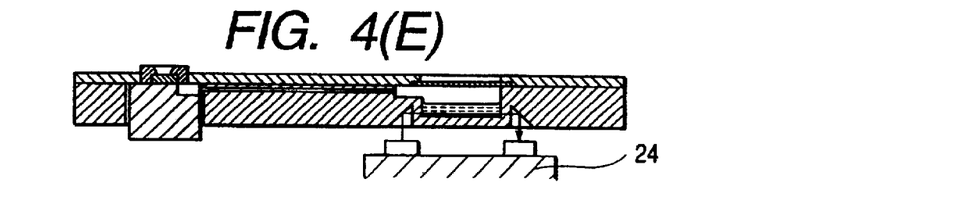

In this instance, as shown in the FIG. 4(E), the optical detector 24 is positioned below the analyzing cassette 11 and a light is irradiated upon the reflection portions 163, which are provided in front and behind the reactor cell 16, so that the light can pass through below the liquid surface within the reactor cell 16, thereby enabling a measurement at a high accuracy without receiving ill influences due to bubbles so on, upon the surface of liquid.

Next, explanation will be given on a third embodiment, by referring to FIGS. 5(A) to (C). The structure of the apparatus according to the present embodiment is almost same to that according to the first embodiment. Only a difference therefrom lies in that an elevating mechanism is further provided in the linear driver portion 21 so that the nozzle 225 of the reagent scale and discharge pump 22 comes in closely contact with the analyzing cassette 1 at the position of the second fine flow passages 13 thereof, directly. Therefore, it is not necessary to provide the cutting window at the position corresponding to the reactor portion on the substrate for testing of the upper substrate of the analyzing cassette 1.

Figure 5B:
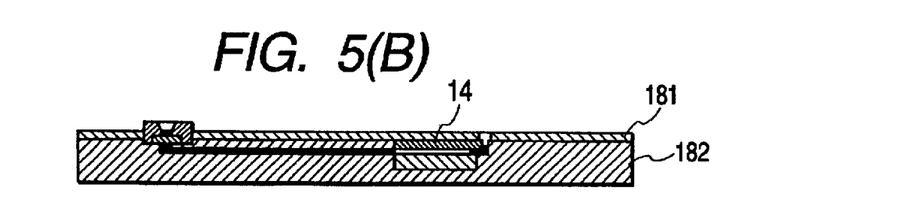
Figure 5C:
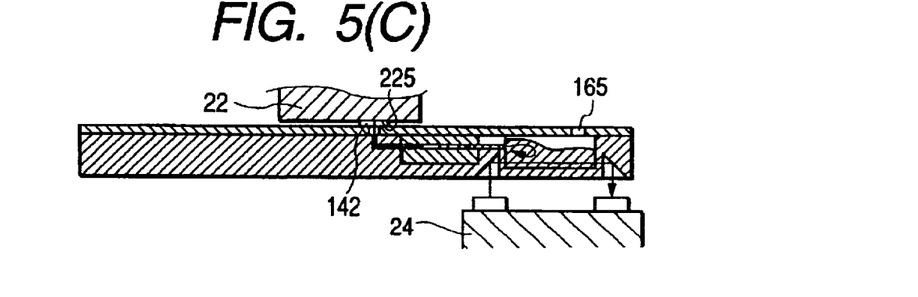

As is shown in the FIG. 5(B), in the same manner as the first embodiment, after sampling a predetermined amount of serum by the slide-type quantity determining valve 14 in the analyzing cassette 1, then the analyzing cassette 1 is inserted into the linear driver portion 21 of the main body 2 of apparatus. According to the present embodiment, the nozzle 225 of the reagent scale and discharge pump 22 comes in touch on the second fine opening 142 of the analyzing cassette 1, directly. When being injected under this condition, as shown in the FIG. 5(C), the reagent 3 is ejected into the reactor cell 16 while pushing the serum therein. Due to the flow formed when being ejected, the reagent 3 and the serum are mixed up with together. The air in the reactor cell 16 is discharged outside through an air opening 165, therefore it will never be compressed or suppressed. After that, in the same manner as in the first and second embodiments, the intensities of spectrum and light emission are measured with using the reflection portions 163 which are provided in front or behind the reactor cell 16.

Explanation will be given on a fourth embodiment by referring to the FIGS. 6(A) and (B). In this fourth embodiment, a piece of a reactor cell 18 is provided on the analyzing cassette 1, which is in a plane-like shape. Also, in place of the main body 2 of the analyzer according to the first embodiment, there is provided a television camera 241 with a high accuracy. Further, the linear driver portion 21 is constructed with a mechanism, which shifts the analyzing cassette 1 on a plane in a two-dimensional manner. The upper substrate 8 is cut off at a portion thereof, opposing to that reactor cell 18.

First, only the serum of blood 4 injected into from the introducing portion 11 spreads on the above-mentioned plane-like reactor cell 18 through the filter 12. In this condition, the analyzing cassette 1 is inserted into the linear driver portion 21 of the main body 2 of apparatus. The linear driver portion 21 shifts the analyzing cassette 1 in the two-dimensional manner, thereby the nozzle 225 of the reagent scale and discharge pump 22 is located at a predetermined position on the plane-like reactor cell 18. Under this condition, a predetermined amount of the reagent 3 is injected. Repeating the same operations, as shown in the FIG. 6(A), different reagents are injected in a manner of a matrix with keeping a predetermined distance therebetween. At each position 185 of the injections, a mixture by diffusing proceeds gradually on a boundary between the reagent 3 which was applied into and the serum therearound. Within such a fine or minute area, since the proceeding of this is governed or controlled by a molecular diffusion depending upon gradation of the concentration thereof, therefore the mixture can be obtained with showing a good reproductivity therewith.

The mixing reaction between the reagent 3 and the serum occurring on the boundary surface thereof is monitored by the television camera 241, so as to measure the process of the reaction. Examining or checking the relationship between the time and a degree of the diffusion in advance, a mixing rate or ratio can be determined therewith, and the concentration of materials dissolved in also can be assumed from the color emission or the light emission therefrom. The analyzing cassette 1 according to the present embodiment is simple in the structure, comparing to that of the other embodiments, thereby enabling to suppress the manufacturing cost thereof. Also, by narrowing the distance between the injections in the matrix manner while reducing the amount of reagents injected, a very large number of spots can be formed thereon, thereby obtaining a feature that a large number of items can be measured at the same time, once.

In the first through fourth embodiments mentioned in the above, the explanation was given only on such the structure, in which the analyzing cassette 1 is mainly constructed with two (2) substrates, however, the upper substrate is not necessarily needed, therefore it may be constructed with the substrate for testing only. In this instance, there is necessities, that the shape of the introducing portion 11 of the substrate for testing, for use in injecting of blood, is fitted with an emission opening at the tip of the injector, and that the reactor cell 16 is covered with a seal or the like over a portion thereof, when being not yet used. However, each substrate of those may be formed from a resin material, such as plastic, etc.

FIG. 7 shows a chemical analyzer system in relation with a fifth embodiment, according to the present invention. The system according to the present invention is constructed by dividing the main body of the analyzer of the first embodiment into a device or apparatus 5 for exclusive use of charging the reagents (i.e., comprising, the reagent bottles, a group of the reagent scale and discharge pump, the linear driver portion, the signal processor portion, and the controller), and an analyzer terminal device 6 for exclusive use of analyzing the analyzing cassette only (i.e., comprising the linear driver portion and the optical detector). The analyzer terminal device 6 are provided in the plural number thereof.

The present system is used in the following manner. First, the reagents 3 are charged into the analyzing cassette 1 by using the exclusive device or apparatus 5 of charging the reagents, in advance, depending upon the requirements of the user thereof. With doing so, it is possible to make or prepare a large number of the analyzing cassettes 1, in a place near to working place of the user, which are customized upon the required items. At hand of each user, there is only the analyzer terminal device 6, therefore only analysis is made by introducing the blood 4 into the analyzing cassettes 1 which were charged and prepared in advance. With such the analysis system, the cost of the analyzer terminal device 6 itself can be reduced down, therefore it is possible to dispose or distribute them at a large number of the users much more. As a matter of course, by connecting between those terminals 6 and the reagent charge device or apparatus 5 through a network, it is possible to monitor an information of supply condition (i.e., in short or excess) of the analyzing cassettes 1, as well as the condition of manufacturing or preparing thereof, and further to make use of improvement in reliability of the analysis values, due to mutual communication of the measured data therebetween.

FIG. 8 shows a sixth embodiment according to the present invention. The basic structure is same to that of the first embodiment. Though being formed in a rectangular or oblong shape in any one of the first to fifth embodiments, however the present embodiment differs from them in an aspect that the analyzing cassette 1 is formed in a disc-like shape. In the present embodiment, as a matter of course, the introducing portion 11 of blood is formed at a center of the disc, and the fine flow passages 13 are provided in radial directions thereof. With applying such the structure, it is sufficient to drive the analyzing cassette 1 rotationally by driving the reagent bottles or containers 23 and the reagent scale and discharge pump 22 linearly, thereby obtaining a high speed of optical detection thereof.

According to the present invention fully explained in the above, there can be provided a small-sized and portable chemical analyzer, with which the reagents can be set or charged freely or arbitrarily by the user(s) depending upon the items of analysis required, and thereby being easy in maintenance thereof without no plumbing for the washing or rinsing liquid and the waste liquid, etc.

What is claimed is:

1. A chemical analyzer having a mechanism for mixing a reagent and a sample liquid to react a component within said sample liquid with the reagent, and enabling measurement of the component, comprising:

an introduction portion for injecting said sample liquid therethrough;

a positioning portion of a carrier, including:

a branched flow passage for distributing said sample liquid injected from said introduction portion;

a plurality of reactor portions for holding said sample liquid flowing down through said branched flow passage and for mixing with said reagent so as to enable reaction thereof; and reagent introduction portions, each being formed at a position corresponding to said reactor portions, and for introducing said reagent into said reactor portion;

a reagent discharge means having a mechanism for discharging different kinds of reagents, one by one, for each of the reactor portions of said carrier;

a position adjustment means having a mechanism for stopping said carrier to be positioned, temporarily, so as to adjust a relative position between said carrier and said reagent discharge means before introducing said reagent into said reactor portions; and a detector portion for detecting the component of said sample liquid after mixing said reagent and said sample liquid.

2. The chemical analyzer, as claimed in the claim 5, wherein a fibrous hygroscopic material is provided in the reactor portion of said carrier.

3. The chemical analyzer, as claimed in the claim 5, wherein a measurement portion for restricting an amount of said sample liquid to be used in a test is provided in said carrier.

4. The chemical analyzer, as claimed in the claim 7, wherein said measurement portion is provided in the branched flow passage between said introduction portion and said reactor portion, while the flow passage from said introduction portion and the flow passage to said reactor portion are separated from, and the respective flow passage is connected in the structure thereof by moving said measurement portion.

5. The chemical analyzer, as claimed in the claim 5, wherein a filer for separating and removing a solid component within the sample liquid is provided between said introduction portion and the branched flow passage or on a portion of the branched flow passage.

6. The chemical analyzer, as claimed in the claim 1, wherein an ion sensor for measuring ion concentration within the sample liquid is provided in one of the reactor portions of said carrier.

7. A chemical analyzer having a mechanism for mixing a reagent and a sample liquid to react a component within said sample liquid with the reagent, and enabling measurement of a concentration of the component, comprising:

an introduction portion for injecting said sample liquid therethrough;

a reagent introduction portion for introducing said reagent therethrough;

a positioning portion of a carrier, having, a filter for filtering said sample liquid injected from said introduction portion, and a reactor portion for distributing the liquid passing through said filter onto a plane, thereby dripping down the reagent introduced from said reagent introduction portion;

a reagent discharge means having a mechanism for discharging different kinds of reagent, one by one, onto different surfaces of the reactor portion of said carrier;

a position adjustment means having a mechanism for stopping said carrier to be positioned, temporarily, so as to adjust a relative position between said carrier and said reagent discharge means before introducing said reagent into said reactor portion; and a detector portion for detecting a component of a mixture liquid in a vicinity of the dripping of said reagent.

8. A chemical analyzing system having a mechanism for mixing up a reagent and a sample liquid, so as to react a targeted component in the sample liquid with the reagent, and enabling measurement of a concentration thereof, comprising:

a positioning portion for a disposal carrier having a region for holding said sample liquid, temporarily, or a plurality of portions;

a carrier stoppage means for stopping said carrier, temporarily;

a sample distribution means for distributing the same sample liquid at a plurality of positions, being different upon said carrier;

a reagent discharge means having a mechanism for distributing different kinds of the reagents, one by one, at a plurality of said sample holding portion, which are distributed on said carrier;

a analyzing terminal having a position adjustment means for adjusting a relative position between said reagent discharge means and said carrier stoppage means; and a reagent filling apparatus for discharging/filling the different kinds of reagents, one by one, to said sample liquid holding portion.

9. A carrier for use in a chemical analyzer, comprising:

an introduction portion for injecting a sample liquid therethrough;

a branched flow passage for distributing said sample liquid injected form said introduction portion;

a plurality of reactor portions, each for holding said sample liquid flowing down through said branched flow passage, so as to enable reaction with a reagent; and a reagent introduction portion, being formed at a position corresponding to said reactor portions, for introducing said reagent into said reactor portions;

wherein said chemical analyzer comprises:

a mechanism for discharging different kinds of reagents for each of the reactor portions of said carrier;

a position adjustment means having a mechanism for stopping said carrier to be positioned, temporarily, so as to adjust a relative position between said carrier and said reagent discharge means before introducing said reagent into said reactor portion; and a detector portion for detecting the component of said sample liquid after mixing said reagent and said sample liquid.

* * * * *